United States Patent [19]

Long et al.

[11] Patent Number: 4,524,215
[45] Date of Patent: Jun. 18, 1985

[54] FLUORINATED ESTERS OF 3,3,4,4-BENZOPHENONE TETRACARBOXYLIC DIANHYDRIDE

[75] Inventors: David J. Long, Stanhope; Bryce C. Oxenrider, Florham Park, both of N.J.

[73] Assignee: Allied Corporation, Morris County, Morris Township, N.J.

[21] Appl. No.: 500,727

[22] Filed: Jun. 3, 1983

[51] Int. Cl.$^3$ ............................................. C07C 69/76
[52] U.S. Cl. ................................. 560/052; 523/200; 523/207
[58] Field of Search ............................................. 560/52

[56] References Cited

U.S. PATENT DOCUMENTS

| | | | |
|---|---|---|---|
| 3,478,087 | 11/1969 | McGrath et al. | 560/52 |
| 4,209,610 | 6/1980 | Mares et al. | 260/40 |
| 4,252,982 | 2/1981 | Oxenrider et al. | 560/87 |
| 4,321,403 | 3/1982 | Oxenrider et al. | 560/87 |

OTHER PUBLICATIONS

Abstract of Japanese Patent Application No. 055056, published 10/22/82 as document No. J57171-761.

*Primary Examiner*—Paul J. Killos
*Attorney, Agent, or Firm*—Richard C. Stewart, II

[57] ABSTRACT

This invention relates to novel fluorinated compounds derived from 3,3′,4,4′-benzophenone tetracarboxylic dianhydride that are useful as surface modifiers for various fibers. The novel compounds contain two fluorinated ester derived from fluorinated alcohols and two esters derived from oxirane compounds.

3 Claims, No Drawings

FLUORINATED ESTERS OF 3,3,4,4-BENZOPHENONE TETRACARBOXYLIC DIANHYDRIDE

DESCRIPTION

BACKGROUND OF THE INVENTION

The present invention relates to compounds derived from 3,3',4,4'-benzophenone tetracarboxylic dianhydride that are useful as surface modifiers of various fibers. The novel benzophenone derivatives contain two fluorinated ester moieties that impart oil repelling characteristics to fibers such as polyamides and polyesters. The novel compounds additionally include two ester moieties derived from oxirane compounds that enable the novel benzophenone compounds to be retained by such fibers after extended use.

Fluorinated pyromellitate surfactants having ester moities similar to those of the benzophenone compounds of this invention are disclosed in U.S. Pat. No. 4,209,610 (Mares et al., 1980). Other patents relating to the pyromellitates of U.S. Pat. No. 4,209,610 include U.S. Pat. No. 4,252,982 (Oxenrider, 1981) wherein an ester solvent is employed as the reaction medium in the production of said pyromellitates and U.S. Pat. No. 4,321,403 (Oxenrider et al., 1981) wherein N-methyl pyrrolidone is employed as the reaction medium solvent. Synthesis of the novel compounds of this invention may be accomplished by employing the general synthetic procedures of the above-described patents.

BRIEF DESCRIPTION OF THE INVENTION

This invention relates to novel compounds having the structure

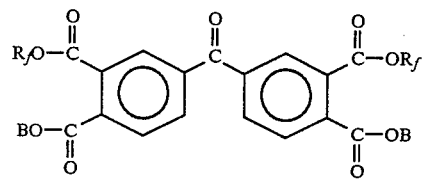

I or

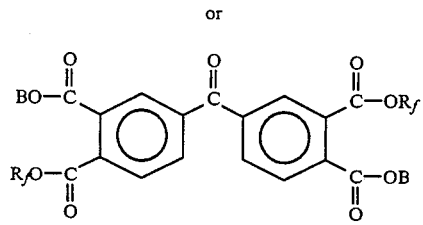

II

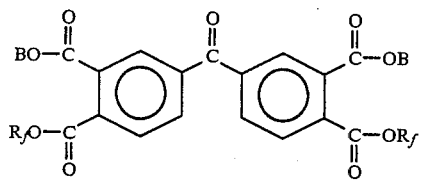

III wherein $R_f$ is AR' with A being alkylene of 2-6 carbons and R' being $CF_3(CF_2)_p$ where p is an integer of 3-15; wherein B is a moiety having the structure

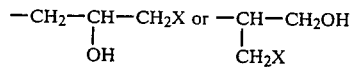

with X being Cl, H, or Br.

The compounds of this invention are useful as surface modifiers for various fibers including polyamides and polyesters such as nylon 6 and poly(ethylene terephthalate).

DETAILED DESCRIPTION OF THE INVENTION

In accordance with this invention, novel fluorinated tetraesters derived from 3,3',4,4'-benzophenone tetracarboxylic dianhydride are provided which are useful as surface modifiers for various fibers. The compounds of the present invention are of the following structures:

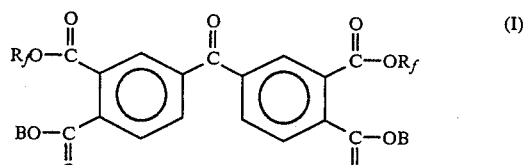

(I)

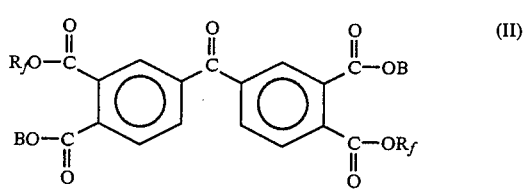

(II)

or

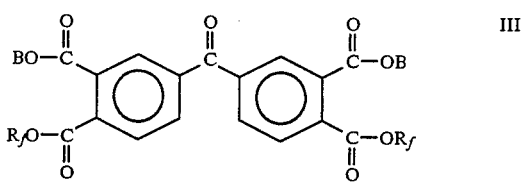

III or mixtures thereof wherein $R_f$ is AR' with A being alkylene of 2-6 carbons and R' being $CF_3\text{-}(CF_2)_p$ where p is 3-15 and wherein B is a moiety having the structure

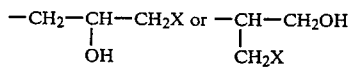

with X being Cl, H, or Br.

In the above structures, the substituents represented by

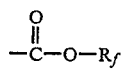

(i.e., fluorinated alkylene moieties) impart oil repelling properties to various fibers such as polyamides and polyesters. Similarly, the substituents represented by

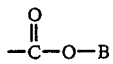

are responsible for the association of the compound with fibers.

In many preferred embodiments of this invention, A in the above-described structure is 1,2-ethylene, 1,2-propylene or 1,4-butylene with 1,2-ethylene being especially preferred. The preferred X moiety is Cl.

Three reactants are employed in the production of the fluorinated benzophenone compounds of the present invention. The first reactant is 3,3',4,4'-benzophenone tetracarboxylic dianhydride. The second reactant is a fluorinated alcohol. The preferred fluorinated alcohols can be represented by the formula $CF_3(CF_2)_pZOH$, wherein Z is alkylene of 2–6 carbons, and p is an integer between 3 and 15, preferably between 3 and 13. In that formula Z is preferably ethylene, 1,2-propylene or 1,4-butylene, and is most preferably ethylene. It is contemplated, and in fact preferred, to use a mixture of alcohols, particularly mixtures with the same Z group such as ethylene, but with varying values for p. A representative commercial mixture of fluorinated alkyl ethanols has the formula $CF_3CF_2(CF_2CF_2)_nCH_2CH_2OH$ wherein n is predominantly 2, 3, 4 and 5 with traces only of n being 1, 6, or 7. The third reactant used in producing the novel compounds of this invention is preferably epichlorohydrin. It may also be the corresponding bromo compound, known as epibromohydrin, or propylene oxide. It will be appreciated that all three of these compounds are three carbon oxiranes with the third carbon being of the formula $CH_2X$ wherein X is Cl, Br or H.

Synthesis of the fluorinated benzophenone compounds of this invention is easily accomplished via a two step synthetic route. The first step involves reacting the fluorinated alcohol with 3,3',4,4'-benzophenone tetracarboxylic dianhydride to produce an intermediate having two fluorinated ester moieties and two free acid moieties. The ratio of the reactants employed in the production of the diester-diacid intermediate should be about two moles of fluorinated alcohol per mole of 3,3',4,4'-benzophenone tetracarboxylic dianhydride. This initial reaction may be conducted at temperatures between about 20° C. and about 80° C. with about 45° C. being the preferred temperature for this step of the synthesis. The length of this initial reaction will range from about 2 hours to about 40 hours depending upon the reaction temperature and whether a catalyst such as triethylamine is employed. Higher reaction temperatures and catalysts will enhance the rate of the reaction and consequently, reduce the time required for the reaction to occur. The described first step of the synthesis of the novel compounds may be illustrated by reaction (1) as follows:

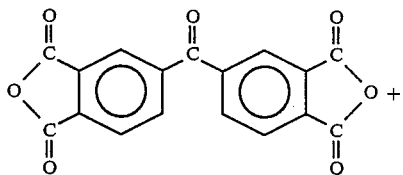

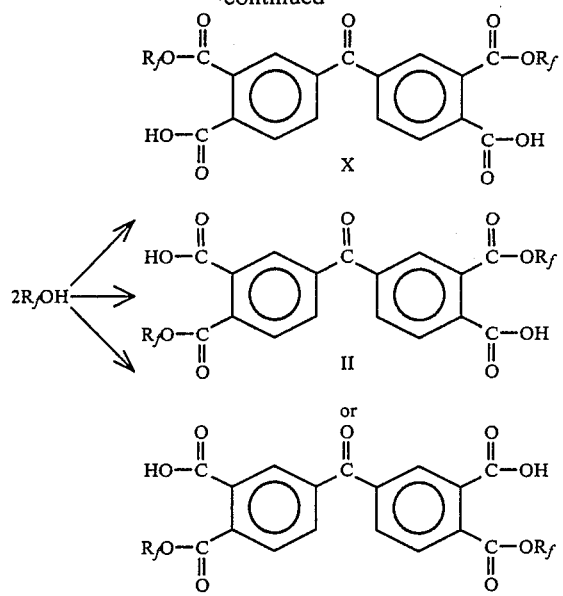

wherein $R_fOH$ is a fluorinated alcohol as described hereinabove.

The diester-diacid represented by structures (IV) (V) and (VI) above depict the three possible isomers. It should be appreciated that the diester-diacid benzophenone intermediate will actually constitute a mixture of the three isomers. It is not necessary to isolate the diester-diacid before proceeding to the next step of the synthesis. However, the diester-diacid intermediate could be isolated if it was desired to do so.

The second and final step of the synthesis of the novel compounds of this invention involves reacting the diester-diacid intermediate with an oxirane compound in an amount sufficient to esterify all of the free acid moieties of the intermediate. This is preferably accomplished by adding the oxirane compound to the reaction medium containing the intermediate and continuing the reaction for a period of time between about 4 and about 20 hours at a temperature between about 20° C. and about 90° C. The preferred temperature range for the second step of the synthesis is between about 55° C. and about 65° C., with the reaction generally being completed in about 4 to 20 hours when this temperature range is employed. In order to monitor the reaction to determine completion of the synthesis, standard titration procedures may be employed. The described second step of the synthesis should preferably be conducted in the presence of a catalyst. Suitable catalysts include triethylamine, tributylamine, lutidene, pyridine and the like, with triethylamine being the preferred catalyst for utilization in the process of this invention.

It should be appreciated that the oxirane compound may react at the number 1 or number 2 carbon of the oxirane during the esterification of the free acid moieties of the intermediate. For example, reaction at the number 1 carbon produces esters having the structure

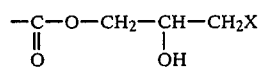

and reaction at the number 2 carbon produces esters having the structure

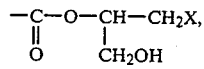

with X being H, Cl, or Br as described hereinabove. However, in most cases the reaction will occur at the number 1 carbon. Nevertheless, some isomers will occur that include an ester moiety formed by the reaction of the oxirane compound at the number 2 carbon.

The above-described two step synthesis may be conducted in any of the organic solvents utilized in forming the compounds of Mares et al., Oxenrider et al., or Oxenrider. Illustrative examples of useful solvents include dimethyl-formamide, N-methylpyrrolidone and aliphatic esters having a boiling point below about 150° C., such as methyl acetate, ethyl acetate, propyl acetate, etc. Other suitable solvents include aliphatic ketones such as methyl isobutyl ketone. The preferred solvent for the practice of this invention is N-methylpyrrolidone.

Synthesis of the novel benzophenone derived surfactants of this invention should preferably be conducted in a dry atmosphere, as for example in the presence of dry nitrogen. Pressure is not critical, with atmospheric pressure being suitable.

Once formed, the benzophenone derived surfactants of the present invention are recovered from the solvent in a manner analogous to that employed in the above Mares et al., Oxenrider et al. and Oxenrider patents. Thus, for example, the entire reaction mixture may be added to a non-solvent such as water when N-methylpyrrolidone is used as solvent, or a volatile ester or ketone solvent may be distilled from the reaction mixture. In either case, it is preferred to wash the initial product at least once with water in order to remove any remaining solvent and/or catalyst and/or unreacted reactants, and especially unreacted oxirane compounds.

The product may then be applied to the polyamide or polyester fiber from an organic solvent such as acetone, methanol or dioxane. It is believed that the novel compounds can be applied to fibers in an emulsion similar to the emulsion described in U.S. Pat. No. 4,192,754 Marshal et al., or in other emulsion systems such as those described in U.S. Pat. Nos. 4,192,754; 4,134,839; 4,190,545; 4,193,880; 4,282,292 and 4,317,726. It is also believed that the compounds may further be applied to the fiber along with other fiber treating agents, and especially spin finishes used to reduce friction of the fiber during processing.

Suitable fibers include poly(caproamide) (nylon 6), poly(hexamethylene diamine adipate) (nylon 6,6) and other poly(diamine dicarboxylate) fibers as well as poly(ethylene terephthalate) (PET). Levels of application are not critical, with levels on a fluoride/fiber basis similar to the above patents being suitable (e.g., 0.050–0.25% fluoride).

Subsequent to fiber application, it is preferred that the treated fiber be annealed to improve the adherance of the treating agent to the fiber. The annealing temperature range is from about 70° C. to about 175° C. However, in many preferred embodiments of this invention, the annealing step is conducted at temperatures between about 100° C. and about 160° C.

EXAMPLE

In performing the reaction described by Example 1, a 250 mL 3-necked round bottom flask was fitted with a stirring bar, thermometer, water condenser, nitrogen inlet and vent. In the example, fluorinated alcohol refers to a mixture of fluorinated alcohols of the formula $CF_3CF_2(CF_2CF_2)_nCH_2CH_2OH$ with n=2, 3, 4, and 5. The fluorinated alcohols contained 2.1 meq OH/g.

EXAMPLE 1

A mixture was formed by dissolving 3,3′,4,4′-benzophenone tetracarboxylic dianhydride (40.2 g, 249.98 meq) and fluorinated alcohol (122.9 g, 238.1 meq) in 80 mL of 1-methyl-2-pyrrolidone. The mixture was placed on a water bath, heated to a temperature of 45° C., and allowed to react for 24 hours. Thereafter, epicholorohydrin (58.6 mL, 755.9 meq) was added to the reaction mixture and the reaction was continued for 18 hours at 55° C. at which time titration indicated that essentially all of the carboxylic acid moieties had been esterified. The reaction mixture was washed with 2.5 L ice water and then dissolved in 3 L chloroform. Product recovery was accomplished by distillation of the solution for removal of chloroform and traces of NMP. An oily product (41.3 g) was recovered. The structure of the product was confirmed by NMR. The surface tension of the product was determined to be 12 dynes/cm by the Zisman procedure.

EXAMPLE 2

PERFORMANCE EVALUATION

Solutions were prepared from the product of Example 1 of 0.25 g of the product in 100 mL acetone. Swatches of nylon 6 (tricot jersey fabric) and poly(ethylene terephthalate) (PET-Dacron 54 heat set spun woven) fabric were dipped in the solutions, air dried for 1 to 3 hours and then annealed for 30 minutes in a circulating oven at selected temperatures. These fabric swatches were then tested for oil repellency by the procedures of AATCC Test No. 118-1966 initially and after being subjected to a number of laundry cycles. The results are displayed in Table I.

TABLE I

| Fiber Anneal Temp (°C.) Laundry Cycles | Nylon 6 | | | | PET | |
|---|---|---|---|---|---|---|
| | 100 | 120 | 140 | 155 | 140 | 155 |
| 0 | 6 | 6 | 6 | 6 | 6 | 6 |
| 1 | 6 | 6 | 6 | 6 | 6 | 6 |
| 2 | 6 | 6 | 6 | 6 | 6 | 6 |
| 3 | 6 | 6 | 5 | 5 | 6 | 6 |
| 4 | 6 | 6 | 5 | 5 | 6 | 6 |
| 5 | 5 | 5 | 5 | 5 | 6 | 5 |
| 6 | 5 | 5 | 5 | 4 | 5 | 5 |
| 7 | 5 | 5 | 4 | 4 | 5 | 5 |
| 8 | 4 | 4 | 4 | 4 | 5 | 5 |
| 9 | 4 | 4 | 3 | 4 | 5 | 5 |
| 10 | 4 | 4 | 3 | 2 | 4 | 5 |
| 11 | 3 | 4 | 3 | | 3 | 4 |
| 12 | 2 | 3 | 2 | | 2 | 2 |
| 13 | | 3 | | | | |
| 14 | | 2 | | | | |

The oil repellency results of the product of Example 1 as illustrated in Table I demonstrate that the novel compounds of this invention are effective surface modifiers. An oil repellancy rating of 4 after 5 laundry cycles is an acceptable rating for many commercial applications. Fibers having the composition of Example 1 applied thereto achieved an oil repellency of 4 after 5 cycles in 6 out of 6 tests. Moreover, an oil repellency rating of 4 was obtained after 9 cycles in 5 out of the 6 tests.

We claim:
1. A compound having the structure
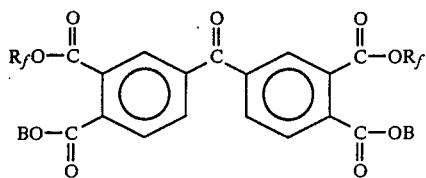
I
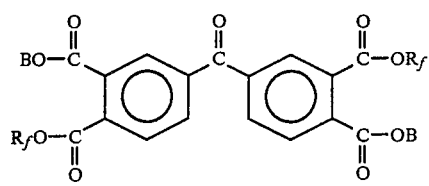
II
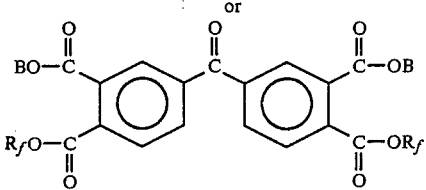
III
wherein $R_f$ is AR' with A being alkylene of 2-6 carbons and R' being $CF_3(CF_2)_p$ where p is an integer of 3-15; wherein B is a moiety having the structure
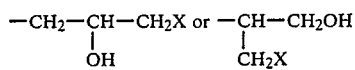
with X being Cl, H, or Br.
2. A compound in accordance with claim 1 wherein A is ethylene.
3. A compound in accordance with claim 1 where X is Cl.